United States Patent
Anderson et al.

(10) Patent No.: US 10,888,375 B2
(45) Date of Patent: Jan. 12, 2021

(54) METHOD AND APPARATUS FOR DERMATOLOGICAL TREATMENT

(71) Applicant: THE GENERAL HOSPITAL CORPORATION, Boston, MA (US)

(72) Inventors: Richard Rox Anderson, Boston, MA (US); Mathew Avram, Boston, MA (US); Wikunda Limpiangkanan, Cambridge, MA (US); William A. Farinelli, Danvers, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 14/413,105

(22) PCT Filed: Jul. 5, 2013

(86) PCT No.: PCT/US2013/049462
§ 371 (c)(1),
(2) Date: Jan. 6, 2015

(87) PCT Pub. No.: WO2014/008481
PCT Pub. Date: Jan. 9, 2014

(65) Prior Publication Data
US 2015/0150629 A1    Jun. 4, 2015

Related U.S. Application Data

(60) Provisional application No. 61/668,726, filed on Jul. 6, 2012.

(51) Int. Cl.
*A61B 18/20* (2006.01)
*A61B 17/064* (2006.01)
(Continued)

(52) U.S. Cl.
CPC ........ *A61B 18/203* (2013.01); *A61B 17/0644* (2013.01); *A61B 17/083* (2013.01);
(Continued)

(58) Field of Classification Search
CPC ............ A61B 17/0466; A61B 17/0644; A61B 17/083; A61B 18/201; A61B 18/203;
(Continued)

(56) References Cited

U.S. PATENT DOCUMENTS 6,178,346 B1 * 1/2001 Amundson .......... A61B 5/0086
348/77
2007/0233207 A1  10/2007 Poirrier et al.
(Continued)

FOREIGN PATENT DOCUMENTS

JP    2010-508964 A    3/2010
JP    2010-521994 A    7/2010
(Continued)

OTHER PUBLICATIONS

International Search Report for International Patent Application No. PCT/US2013/049462 dated Nov. 7, 2013.
(Continued)

*Primary Examiner* — Jonathan T Kuo
(74) *Attorney, Agent, or Firm* — Hunton Andrews Kurth LLP

(57) ABSTRACT

Exemplary methods and systems can be provided for resurfacing of skin that include formation of a plurality of small holes, e.g., having widths greater than about 0.2 mm and less than about 0.7 mm or 0.5 mm, using ablative electromagnetic radiation, e.g., optical energy. An optically transparent plate or window can be pressed over a surface of the skin tissue as the holes are ablated to disrupt formation of a thermal cuff around the holes. Compressive or tensile forces can then be applied to the treated region of the skin tissue as
(Continued)

the damage heals to facilitate hole closure and provide enhanced and/or directional shrinkage of the treated skin area.

19 Claims, 7 Drawing Sheets

(51) Int. Cl.
| | |
|---|---|
| *A61B 17/08* | (2006.01) |
| *A61B 18/00* | (2006.01) |
| *A61B 17/00* | (2006.01) |
| *A61B 18/22* | (2006.01) |
| *A61B 17/04* | (2006.01) |

(52) U.S. Cl.
CPC ......... *A61B 17/0466* (2013.01); *A61B 18/201* (2013.01); *A61B 2017/005* (2013.01); *A61B 2017/00761* (2013.01); *A61B 2017/00765* (2013.01); *A61B 2018/0047* (2013.01); *A61B 2018/00577* (2013.01); *A61B 2018/2211* (2013.01)

(58) Field of Classification Search
CPC .... A61B 2017/005; A61B 2017/00761; A61B 2017/00765; A61B 2018/0047; A61B 2018/00577; A61B 2018/2211
USPC ............. 606/9, 33, 131, 151, 167, 185, 186, 606/213–233
See application file for complete search history.

(56) References Cited

U.S. PATENT DOCUMENTS

| | | | |
|---|---|---|---|
| 2007/0239236 A1 | 10/2007 | Manstein | |
| 2008/0033334 A1* | 2/2008 | Gurtner | ................... A61L 15/42 602/50 |
| 2008/0306471 A1* | 12/2008 | Altshuler | ............... A61B 5/441 606/10 |
| 2012/0226214 A1* | 9/2012 | Gurtner | ................... A61F 13/00 602/53 |
| 2012/0226268 A1* | 9/2012 | Liu | ....................... A61B 18/203 606/9 |
| 2013/0110026 A1* | 5/2013 | Jackson | ............ A61F 13/00034 602/53 |
| 2014/0039523 A1* | 2/2014 | Austen | ................. A61B 17/205 606/131 |

FOREIGN PATENT DOCUMENTS

| | | |
|---|---|---|
| JP | 4769580 B2 | 9/2011 |
| JP | 2012-510318 A | 5/2012 |
| JP | 2013-525070 A | 6/2013 |
| RU | 2077274 | 4/1997 |
| WO | WO 2004/086947 | 10/2004 |
| WO | WO 2010/114987 A2 | 10/2010 |
| WO | WO 2011/050318 A2 | 4/2011 |
| WO | WO 2011/123218 A1 | 10/2011 |
| WO | 2011/139912 A1 | 11/2011 |
| WO | 2012/070556 A1 | 5/2012 |

OTHER PUBLICATIONS

International Written Opinion for International Patent Application No. PCT/US2013/049462 dated Nov. 7, 2013.
Extended European Search Report for European Application No. 13813933.2 dated Mar. 29, 2016.
Japanese Notice of Allowance for Japanese National Phase Application No. 2015-520709.
Notice of Reasons for Rejection dated Jan. 17, 2017 for Japanese National Phase Application No. 2015-520709.
Communication pursuant to Article 94(3) EPC dated Jan. 30, 2019 for European Application No. 13813933.2.
Communication pursuant to Articte 94(3) EPC dated Sep. 18, 2019 for European Patent Application No. 13813933.2.
Communication Pursuant to Article 94(3) EPC dated Aug. 5, 2020 for European Patent Application No. 13813933.2.

* cited by examiner

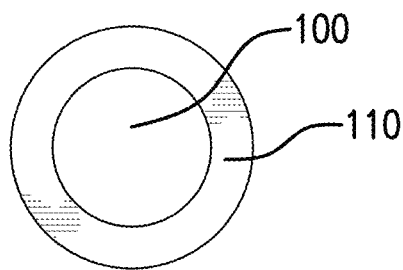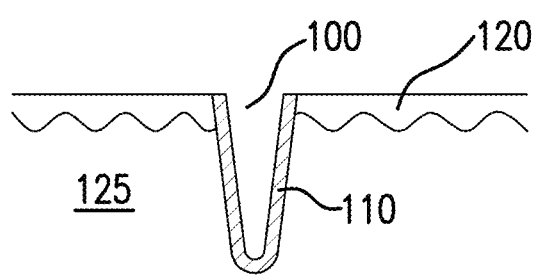
FIG.1A                FIG.1B
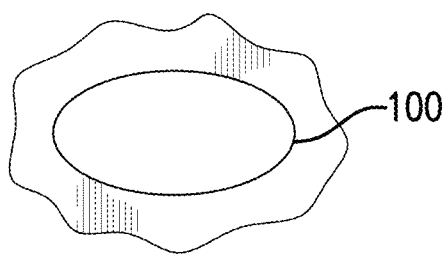
FIG.1C                FIG.1D
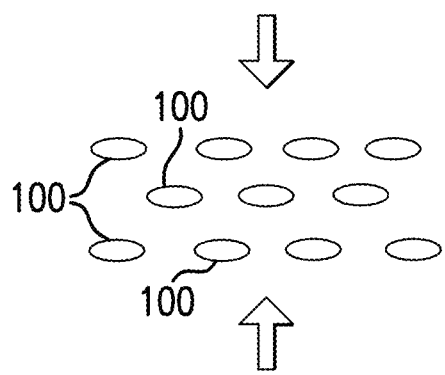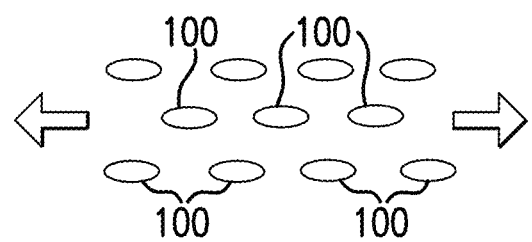
FIG.1E                FIG.1F
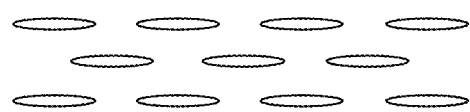
FIG.1G

METHOD AND APPARATUS FOR DERMATOLOGICAL TREATMENT

CROSS-REFERENCE TO RELATED APPLICATION(S)

The present application relates to and claims priority from International Patent Application No. PCT/US2013/049462 filed Jul. 5, 2013, and from U.S. Provisional Patent Application Ser. No. 61/668,726 filed Jul. 6, 2012, the entire disclosures of which are incorporated herein by reference in their entireties.

TECHNICAL FIELD

The present disclosure relates to cosmetic methods and systems for improved laser-based fractional resurfacing of skin tissue and similar procedures, specifically, such methods and systems that facilitate enhanced and/or directional reduction in skin area or reduction of wrinkles.

BACKGROUND

There is an increasing demand for repair of or improvement to skin defects, which can be induced by aging, sun exposure, trauma, surgical procedures, heredity, and the like. Skin loses its tone and smooth texture as it ages, commonly developing wrinkles and laxity. This can be further compounded by photodamage and other effects such as, e.g., scarring from trauma, age-related rhytides, and striae. Aged skin is characterized by a flattened dermal-epidermal junction, thinning epidermis and dermis, less fibrous collagen, and alterations in elastin organization. Skin rejuvenation therapies work to remove these damaged tissues and/or and stimulate the growth of new, healthy collagen, elastic fibers and skin cells and thereby improve the appearance of the skin.

Reduction in the appearance of wrinkles is an objective of many dermatological procedures and treatments. Certain treatments may be used to improve the appearance of skin by irradiating the skin with electromagnetic energy, which can lead to beneficial responses to improve the treated skin condition. A common procedure for skin rejuvenation, i.e., laser resurfacing, uses light energy to heat and damage the upper dermis. However, laser resurfacing has a poor side effect profile, with many patients experiencing prolonged erythema, scarring and dyspigmentation.

Ablative fractional thermolysis, or fractional resurfacing, is a treatment that uses laser light sources, such as erbium or carbon dioxide ($CO_2$) lasers, to vaporize a plurality of microscopic holes within skin. The diameter of such holes are typically less than about 1 mm, e.g., about 300 microns or less, and can be formed with little or no bleeding. The hole depths are typically about 1-3 mm, such that they extend deeply into or through the human dermis, which is of similar thickness. Such small holes, which are surrounded by healthy tissue, tend to heal rapidly without producing visible damage or scarring. The process of ablation or tissue vaporization removes tissue and generates heat that denatures the surrounding collagen layers. Fibril bundles in the collagen shrink and can tighten the dermal layer. The denatured collagen can also heal and, in combination with other thermal damage, stimulate the synthesis of new collagen, which can produce desirable cosmetic results. For example, the shrinkage and tightening in the skin can improve the appearance of wrinkles and loose skin. Such fractional resurfacing treatments tend to produce general tightening of the skin that has no directional preference or bias.

The fraction of skin surface covered by holes in an ablative fractional thermolysis treatment can be as large as about 50%, and typical surface coverage tends to be in the range of about 10%-30%. However, most of the ablated tissue tends to grow back during the healing process, and the observed reduction of skin area after treatment by ablative fractional thermolysis is much less than that which would result based on the amount of surface tissue removed. Further, the slight amounts of shrinkage tend to be uniform and not directional. Thus, it appears that the many small holes created through skin during ablative fractional resurfacing become almost completely filled in with new skin tissue, such that the skin area is not greatly reduced although some firming of the skin may be observed. This process of filling in has been observed in histological studies of human skin following fractional laser resurfacing.

It has also been observed that a small "cuff" or layer of thermally damaged tissue remains around the microscopic holes created during fractional ablative laser resurfacing or other procedures involving laser ablation of skin tissue. This layer can be mechanically stiff and difficult to collapse, and may inhibit closure of the ablated holes. The holes then fill with fluid and other tissue exudates after the ablation occurs, which can further limit the extent of areal tissue shrinkage.

Many wrinkles tend to present on certain parts of the body with a general orientation, such as wrinkles extending laterally from the corners of the eyes or mouth, or along the neck beneath the jaw. Directional shrinkage of skin can be achieved by removing elongated areas of skin in an appropriate shape, and then joining the edges of remaining skin (e.g. with sutures) to "pull" the skin back in a particular direction. Such procedures, as used in conventional facelifts, create large scars that must be carefully located, and may generate some unnatural-looking shrinkage in response to the large-scale removal and repositioning of the skin. If skin on the face or neck itself could be removed in a way that decreases the area of skin, with preference to one or more local directions for reduction of skin area, and without visible scarring, the result would be a more natural appearance while still removing unwanted sagging or redundant skin.

It has been proposed to remove smaller portions of skin, e.g. on the order of a few millimeters wide, and to close the resulting holes with sutures or the like to produce a more controlled reduction of skin area. Such holes should be elongated (e.g. lenticular or elliptical in shape) to facilitate their closure by approximating their longer edges and avoid the formation of dog-ears when they are collapsed. However, such holes are still large enough to produce visible markings when healed, and full healing time may require a few weeks. Further, closure of such holes is a skill-intensive procedure that would require manipulation such as individual suturing or manual, even approximation followed by application of an adhesive coating such as a cyanoacrylate adhesive to keep the holes closed until they heal. Such hole closure procedures would be time-intensive and lead to visible scarring.

Accordingly, there may be a need for a relatively simple, robust, and safe cosmetic method and system that can be optical in nature, and would overcome at least some of such exemplary deficiencies described above, and that can be configured to produce fractional damage in biological tissue that leads to directional reduction of skin surface area without causing visible scarring.

SUMMARY

The present disclosure relates to exemplary embodiments of safe cosmetic methods and systems for generation of a plurality of small holes, e.g., microregions of damage, in biological tissue, such as skin, using an ablative laser or other ablative electromagnetic radiation, or optical energy, and for manipulating the treated skin to generate a cosmetically desirable reduction of skin area that can be enhanced and/or that has a particular or preferred direction. Such exemplary holes can have a width or diameter that is less than 1 mm, e.g., between 100 and 500 microns. In certain embodiments, the width or diameter of the holes can be less than 300 microns, or between about 0.2 mm and 0.7 mm, or preferably between about 0.2 mm and 0.5 mm, as measured along the tissue surface. Such holes can extend from the skin surface into, or preferably through most of or the entire thickness of, the dermis. The fractional area of skin removed by formation of such holes in a treatment region can be between about 5% and 50%, or between about 10% and 30%. Formation of ablated holes in this sub-millimeter size range and areal coverage is well-tolerated by the body, with minimal risk of scarring, infection, or other complications.

In certain exemplary embodiments of the present disclosure, the holes can be formed by directing optical energy onto a plurality of locations in the region of skin to be treated, e.g. in the form of one or more collimated or focused beams, such that the optical energy is sufficiently intense to ablate biological tissue. The size and depth of the holes formed can be controlled by a variety of parameters, including the total energy or fluence directed onto each location, the wavelength(s) of optical energy used, the beam width or diameter, duration of energy application to a particular location, etc.

The ablative optical energy can be provided by a laser or other source that is capable of generating energy of sufficient intensity and appropriate wavelength(s) to ablate biological tissue. In certain exemplary embodiments, the laser can be a $CO_2$ laser, an erbium laser such as an Er:YAG laser, or an excimer laser.

In certain further exemplary embodiments of the present disclosure, an optically transparent plate or window that can be pressed onto at least a portion of the treatment region while the holes are being ablated. Such window can facilitate mechanical or other disruption of any thermal cuff that may form around the ablated holes by preventing or inhibiting by-products formed during ablation from escaping from the holes.

An exemplary embodiment of a cosmetic method according to the present disclosure can be provided that can include an ablation of a plurality of holes in a region of skin as described above, and then an application of tensile and/or compressive stresses in a direction generally along the surface of the skin to the treated region during subsequent healing process. Such stresses can enhance overall reduction in the treated region and/or provide a directional bias to the resulting shrinkage. The applied stresses can be maintained in the treated region until the holes have substantially closed and/or tissue regrowth has been effectively modified, e.g., between about 4-6 days or longer. In certain exemplary embodiments, this time period may be much shorter, e.g., on the order of several minutes or hours, if a tissue adhesive, glue, or the like is used to facilitate hole closure.

According to one exemplary embodiment of the present disclosure, a pre-stretched or heat-shrinkable film can be adhered to the surface of the treated region after the holes are formed. The resulting compressive stresses can enhance hole closure in the direction of the applied stresses and/or affect the orientation of collagen or other structures that grow or evolve as part of a healing response in the tissue surrounding the small holes. A rigid film, plate, or other object can optionally be adhered over the stretched film to provide mechanical stability and maintain deformation of the treated region during the primary healing process.

In further exemplary embodiments of the present disclosure, compressive stresses can be generated in the treated region of skin by applying one or more surgical staples, elastic clips and/or sutures to the area. The staples and/or sutures are preferably large, such that they span several of the formed holes, and optionally the entire treated region. In certain embodiments, a plurality of staples or sutures can be applied to a single area at different orientations, to provide omnidirectional compressive stresses that can enhance hole closure and overall shrinkage of the treated region as compared to a similarly-treated region without the applied stresses.

According to other exemplary embodiments of the present disclosure, compressive stresses can be generated by applying a shrinkable material to the skin surface after the holes are formed therein. The shrinkable material can include, e.g., a heat-shrink film adhered to the skin surface and then heated, a liquid layer that can polymerize or react to form an adherent film that reduces in size as it forms, cures or ages, etc.

In other exemplary embodiments, a photoactivated adhesive can be applied to the surface of the treated region, and a compressive or tensile stress can be generated in the region while directing alight energy onto the region to activate the adhesive. The photoactivated adhesive can include, e.g., rose bengal or any other photoactivated biological adhesive known in the art.

According to still further exemplary embodiments of the present disclosure, tensile stresses can be generated in the treated region of skin by stretching the treated region in one or more directions along the skin surface, which can facilitate hole closure and shrinkage in a direction orthogonal to the direction of the applied tensile stress. Such tensile stresses can be manually generated and then maintained, e.g., by adhering a rigid film, plate, or other object to the stretched area of skin.

According to additional exemplary embodiments of the present disclosure, a system can be provided for generating a plurality of holes in a region of skin that includes a source of optical energy, e.g., an ablative laser, and an optical arrangement, that is configured or adapted to ablate a plurality of small holes in a treatment region of skin or other biological tissue as described herein. The exemplary system can include an optically transparent plate or window that can be pressed onto the treatment region while the holes are being ablated. Such window can facilitate a disruption of any thermal cuff that may form around the ablated holes by preventing or inhibiting by-products formed during ablation from escaping from the holes. For example, this window can generate (or facilitate a generation of) an increased pressure within the ablated hole arising from formation of high-temperature vaporized by-products, and the pressure in an ablated hole may cause mechanical disruption of the surrounding rigid thermal cuff.

In certain exemplary embodiments of the present disclosure, the lower surface of the window adapted, configured or structured to contact the skin or tissue surface may be flat. According to further exemplary embodiments of the present disclosure, this lower surface may be rounded, e.g., cylindrical, spheroidal or ellipsoidal in shape. Such rounded or curved shape may facilitate application of pressure over a location where a hole is being ablated, e.g., when the optical energy is directed to a location in the treatment region that is directly beneath the contact area of the window.

The exemplary system can further include a compression arrangement capable of applying a compression device or substance to deform the treated region after the holes are formed therein. For example, the compression arrangement can include a surgical stapler, a suturing device, an applicator capable of applying an elastic clip arrangement, a stretched film, a curable/shrinkable liquid, or the like onto, into, or adjacent to the treated region.

The herein described exemplary embodiments pertain to a cosmetic method and apparatus. It shall further be noted that the herein described cosmetic method has been tested, and is a safe and routine procedure that can be practiced in beauty parlors or other settings. The presented exemplary method is a minimally-invasive method. Moreover, the exemplary method can be safe as it does not present a substantial health risk, and does not require professional medical expertise to be performed. No clinician is needed to perform any of the procedures according to the exemplary embodiments of the method described herein, and little or no risk, much less a health risk, is presented for a person being treated with said cosmetic method if standard cleanliness and sterilization procedures are employed, as shall become apparent from the following description.

Synergetic effects may arise from different combinations of the features and embodiments described herein, although all such combinations might not be described in detail. Further, it shall be noted that all embodiments of the present disclosure concerning a method or system according to the exemplary embodiments of the present disclosure, might be carried out with the order of the steps or procedures as described, nevertheless this has not to be the only and essential order of the steps of the procedures of the method and the system. All and any different orders and combinations of the steps and procedures are herewith described.

These and other objects, features and advantages of the present disclosure will become apparent upon reading the following detailed description of exemplary embodiments of the present disclosure, when taken in conjunction with the appended drawings and claims.

BRIEF DESCRIPTION OF THE DRAWINGS

Further objects, features and advantages of the present disclosure will become apparent from the following detailed description taken in conjunction with the accompanying figures showing illustrative embodiments, results and/or features of the present disclosure, in which:

FIG. 1A is a top view of a round hole with associated thermal cuff that can be formed in skin tissue using an ablative procedure according to an exemplary embodiment of the present disclosure;

FIG. 1B is a schematic side view of the ablated hole shown in FIG. 1A;

FIG. 1C is a top view of an elongated hole that can be formed in skin tissue in accordance with further exemplary embodiments of the present disclosure;

FIG. 1D is a top view of a lenticular-shaped hole that can be formed in skin tissue in accordance with still further exemplary embodiments of the present disclosure;

FIG. 1E is a schematic top view of a treatment region of skin containing a plurality of ablated holes with an exemplary compressive stress applied to the surface thereof;

FIG. 1F is a schematic top view of the treatment region of skin containing the plurality of ablated holes with an exemplary tensile stress applied to the surface thereof;

FIG. 1G is a schematic top view of the treatment region of skin containing the plurality of ablated holes after such holes have closed in a preferred direction;

Figure 2A:
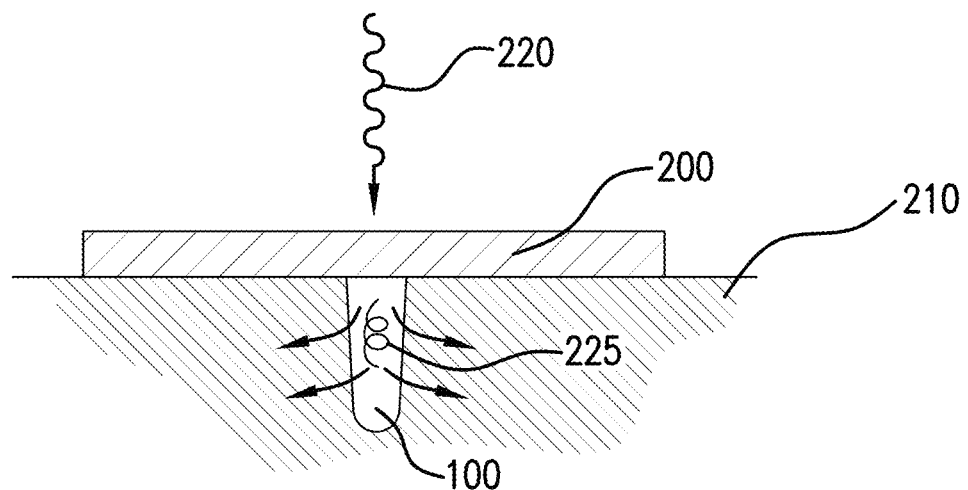
FIG. 2A is a schematic side view of the hole being ablated in a biological tissue such as skin with an optically transparent plate applied to the tissue surface, in accordance with exemplary embodiments of the present disclosure.

Throughout the drawings, the same reference numerals and characters, unless otherwise stated, are used to denote like features, elements, components, or portions of the illustrated embodiments. Similar features may thus be described by the same reference numerals, which indicate to the skilled reader that exchanges of features between different 5 embodiments can be done unless otherwise explicitly stated. Moreover, while the present disclosure will now be described in detail with reference to the figures, it is done so in connection with the illustrative embodiments and is not limited by the particular embodiments illustrated in the figures. It is intended that changes and modifications can be made to the described embodiments without departing from the true scope and spirit of the present disclosure as defined by the appended claims.

DETAILED DESCRIPTION OF EXEMPLARY EMBODIMENTS

Exemplary embodiments of the present disclosure relate to cosmetic methods and apparatus for closing a plurality of small skin holes generated by an ablative fractional resurfacing procedure or similar procedure, optionally in an exemplary direction, that can result in a reduction of skin surface area that is enhanced and/or locally directional, without visible scarring.

According to certain exemplary embodiments of the present disclosure, a plurality of small holes 100, such as the hole 100 shown in the top view of FIG. 1A, can be formed by an ablative procedure using directed optical energy, as described in more detail below. The width or diameter of the holes 100 can be less than 1 mm, e.g., between 100 and 500 microns. In certain embodiments, the width or diameter of the holes 100 can be less than 300 microns, or between 200 microns and 700 microns, or preferably between 200 microns and 500 microns. The hole sizes can be determined by the diameter or size of the beam(s) of collimated or focused ablative radiation (e.g., optical energy) used to ablate the holes. The small sizes of such holes can avoid the formation of visible markings or scars after the surrounding tissue heals. Forming holes in this size range is also well-tolerated and safe, because of the very small size of the damaged regions formed and the presence of undamaged adjacent tissue to promote rapid healing.

The holes 100 shown in FIG. 1A is substantially round. Other hole shapes can be formed in accordance with certain exemplary embodiments of the present disclosure, such as elongated, elliptical, or lenticular-shaped holes 100. For example, the holes 100 can be ovoid in cross-sectional shape, e.g., similar to that shown in FIG. 1C. In further exemplary embodiments, the holes 100 can have a lenticular shape, e.g., such as that shown in FIG. 1D. For example, the aspect ratio of the lenticular hole 100 can be, e.g., about 3:1, and the angle at which the curved sides meet can be about 30 degrees. This ratio (or an aspect ratio close to this) and geometry can facilitate closure of the hole 100 by reducing associated stresses or deformations in the surrounding tissue. Although the shape of an actual lenticular hole 100 formed in soft tissue may not have precisely smooth edges and sharp corners, a hole shape approximating that shown in FIG. 4B can facilitate closure of the formed holes as they heal.

In one exemplary embodiment, elongated holes 100, such as those shown in FIGS. 1C and 1D, can be formed in tissue by stretching the tissue in a direction, and then forming the holes 100 in the tissue, e.g., using a beam of ablative radiation 220 (e.g., a beam of optical energy) having a substantially circular cross section, or a similar device or technique. Upon allowing the tissue to relax, the hole 100 will not be quite round. In a further exemplary embodiment, the radiation beam 220 can be shaped to generate non-circular holes 100 in tissue. For example, the beam 220 can be directed through one or more lenses (e.g., a cylindrical lens) or via other optical arrangement(s) that can alter the cross-sectional shape of the beam 220. In further exemplary embodiments, the beam 220 can have a small diameter (e.g., less than 100 microns) and a translator arrangement can be provided to scan or direct the beam 220 to ablate holes 100 having desired shapes.

In general, the precise shape of the holes 100 may not be important and/or critical, and may not significantly affect the subsequent directional shrinkage or closure behavior, because the small size scale (e.g., 0.7 mm or less) can facilitate an approximation of the hole edges in any desired direction without generating unwanted effects such as "dog ears" or misalignments when they close and heal together.

An exemplary layer or "cuff" of thermally-damaged tissue 110 is also shown in FIG. 1A. The thickness of this layer is generally about 150 microns or less, depending on the type of laser and ablative conditions used, and it can be mechanically rigid. A side view of the hole 100 is shown in FIG. 1B, where the hole extends into the skin through the epidermis 120 and into the dermis 125. The cuff 110 surrounds most or all of the hole surface, even below the skin, and is formed during the ablative process.

During a conventional ablative fractional thermolysis procedure, steam and/or other vaporized materials can be generated from the rapid absorption of radiation energy by the tissue. These vaporized by-products typically are emitted or ejected freely from the holes 100 as they rapidly expand during heating of the tissue.

Because the cuff 110 can inhibit closure of the holes 100 after a fractional thermolysis procedure, it may be desirable to generate holes 100 that are not surrounded by such a rigid, continuous layer. In one embodiment of the present disclosure, a clear plate 200 can be provided on the surface of the skin 210, as shown in FIG. 2A. A beam of ablative radiation 220 can be directed onto particular locations in the treatment region of the skin 210 through the plate 200 to form the holes 100.

The plate 200 can be formed of a material that is substantially transparent (e.g., exhibits a low absorption coefficient) to the particular type of ablative radiation or optical energy being applied. For example, zinc selenide (ZnSe) is substantially transparent to the electromagnetic radiation produced by a typical $CO_2$ laser, which has a wavelength of about 10,600 nm. Another material that may be used in certain embodiments is germanium. In a further exemplary embodiment, a plate or window 200 made of sapphire can be used with an erbium ablative laser, which emits radiation having a wavelength of about 2,940 nm. Other materials can be used to form the plate 200, and can be selected based on the characteristics of ablative radiation 220 (e.g., the wavelength(s) of such radiation 220) used for the ablative procedure.

The plate 200 can be held or maintained on the skin surface with a sufficient pressure to inhibit or prevent vaporized materials 225 from escaping through the top of the hole 100. Accordingly, the vaporized materials 225 can be forced deeper into the tissue 210, e.g., through the lateral sides of the hole, indicated by the arrows in FIG. 2A, as their expansion increases pressure within the hole 100 that is blocked by the plate 200. The constrained vaporized materials 225 can disrupt and/or break up the thermally-damaged layer 110 that is typically formed during the ablation process. The plate 200 can be provided together with the source of ablative radiation or an optical arrangement such as a fiber optic delivery arrangement, e.g., in a handpiece or housing, as an apparatus that is configured to ablate the small holes 100 in the tissue 210, while constraining vaporized by-products from exiting the top of the hole(s) 100 as it is (or they are) formed, as described herein.

Figure 2B:
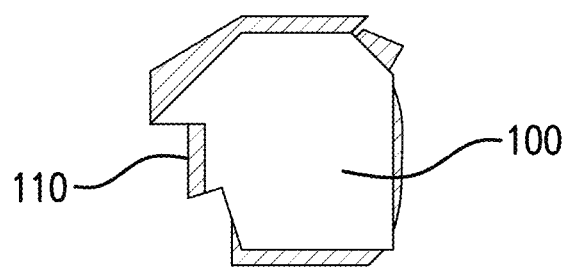
FIG. 2B is a schematic top view of the ablated hole such as that shown in FIG. 1A, where the thermal cuff is disrupted after providing a plate over the hole while it is formed as shown in FIG. 2A.

For example, microscopic holes 100 produced by the ablation of the tissue 210 (e.g., skin) with the plate 200 held onto the tissue surface can have an irregular shape such as that shown in FIG. 2B. Unlike the substantially uniform cuff of material 110 that can be formed during unconstrained ablation of holes 100 in skin tissue, e.g., as shown in FIG. 1A, the thermally-damaged material 110 shown in FIG. 2B can have a more irregular shape, varying thickness, and can be broken up or missing along portions of the hole perimeter. The lack of a continuous cuff of thermally-damaged material 110 around the edges of the hole 100 can facilitate closure of the hole 100 after it has been formed, and lead to increased shrinkage of skin tissue, as described herein.

According to a further exemplary embodiment, the shape of the lower surface of the plate 200 that contacts the treatment region can be curved, e.g., having a local shape that is cylindrical, spheroidal, ellipsoidal or ovoidal. Alternatively, the plate 200 can be formed with a profile that is configured to conform to the local shape of the tissue surface. The plate 200 can have a flat side facing towards the source of ablative radiation. Other plate geometries can be used that provide a rounded surface that contacts the tissue surface. For example, the plate 200 can be provided as a cylindrical roller that can be rolled over the tissue surface, while the radiation beam 220 is directed into the tissue where it contacts the roller surface to ablate holes beneath the contact point.

Such non-planar plate geometries can provide a compressive force on the tissue surface that facilitates pressure buildup within the holes 100 as they are formed, as described herein, to disrupt the formation of a continuous rigid cuff of thermally-damaged tissue 110. The curved surface can also provide some degree of stretching of the tissue near the surface in a direction perpendicular to the longitudinal axis of the cylinder or half-cylinder having a flat upper surface. The radiation beam 220 can be scanned along the longitudinal axis of the cylinder where it contacts the tissue surface to form a row of holes 100. The cylinder and beam 220 can be translated along the surface of the tissue, e.g., in a direction perpendicular to the longitudinal axis of the cylinder, to generate a plurality of rows of holes 100, and form an overall distribution of ablated holes 100 in the tissue. The holes 100 formed in this manner can be elongated, even if formed using the ablative beam 220 having circular cross-section, when the plate 200 is removed from the tissue and the tissue is allowed to relax.

In still further exemplary embodiments, a patterned mask can be provided, and radiation energy (e.g., a wide laser beam or other ablative optical energy) can be scanned over the mask, such that holes 100 can be ablated in skin tissue beneath openings in the mask in the approximate shape of the openings. The mask can be provided, for example, on an upper or lower surface of the plate 200, or in other configurations that will block portions of a radiation beam 220 scanned over the tissue being treated.

The type of laser used to ablate the holes 100 can affect the extent of thermal cuff 110 that may form. For example, a conventional $CO_2$ laser can produce a thermal cuff 110 that can hinder hole closure. Accordingly, it may be preferable to use an optically clear plate 200, e.g., as illustrated in FIG. 2A, to disrupt any such thermal cuff 110 that may form around the ablated holes 100. In certain exemplary embodiments, an erbium laser, e.g. an Er:YAG laser, can be used to ablate the holes. Erbium lasers can ablate tissue while producing a smaller thermal cuff 110 at the edges as compared to a $CO_2$ laser. According to further exemplary embodiments, an excimer laser or a femtosecond ablative laser can be used to form the holes 100. Such lasers can ablate holes 100 while forming a still smaller or negligible thermal cuff 110 as compared to, e.g., a $CO_2$ laser. The use of a plate 200 when ablating the holes 100, as described herein, can improve the hole closure and healing process that may be inhibited by the presence of a thermal cuff 110.

In certain exemplary embodiments of the present disclosure, the treatment region can be cooled prior to and/or during ablative formation of the holes 100. The cooling can be achieved using any methods known in the art, e.g., applying a cooled plate or other object to the surface of the treatment region prior to and/or during the ablation process, using a cryospray to cool the surface of the treatment region prior to ablation of the holes 100, etc. Such exemplary cooling of the skin tissue can reduce the size or thickness of the thermal cuff 110 that can form as compared to ablation of uncooled tissue under otherwise similar conditions.

According to certain exemplary embodiments of the present disclosure, a plurality of holes 100 can be formed such that the fraction of surface area ablated is generally between about 5% and 50%, e.g., between about 10% and 30%. The holes 100 can be formed randomly, or in various patterns. For example, the ablating holes 100 in the skin or other tissue in a pattern of staggered rows, such as that shown in FIGS. 1E and 1F, can facilitate closure of the holes 100 during healing. This pattern of the holes 100, or any other desired pattern or arrangement of the holes 100, can be formed using a variety of techniques. For example, the holes 100 can be formed by scanning a pulsed laser beam along the rows, with a control arrangement provided to pulse the beam at appropriate times while being scanned using a conventional optical scanning arrangement to form the desired pattern of the holes 100. Alternatively, a mask can be provided, as described herein, that has the shape of the desired ablation or hole pattern. In certain embodiments, the spatial distribution of holes can be substantially random.

The density and/or proximity of the holes 100 can also be varied in different regions of the tissue being treated. For example, the holes 100 can be spaced further apart in the peripheral areas or edges of a particular treated region. Such "feathering" of the removed tissue volume can facilitate a smoother or gradual transition between the shrunken or tightened skin within the treatment region and the untreated region of tissue surrounding it. However, such "feathering" or density gradients of the holes 100 may not be particularly important for obtaining a continuous directional shrinkage over the treated region, because the large number of small holes 100 can adjust to gradients in skin deformation during the subsequent healing process. For example, the large number and moderate to high density of microscopic holes 100 can accommodate macroscopic gradients in shrinkage with only very minor local differences in the closure and healing behavior of each individual hole 100. Such exemplary gradients and directionality can be produced, e.g., by the exemplary manipulation of the treated region after the holes 100 are formed, as described herein below.

The particular shape and size of the treated region in which the holes 100 are formed is arbitrary, and can be selected based on the areas of skin that may benefit from the exemplary methods described herein. Such exemplary methods can be effective over both small regions (e.g. on the order of a square cm or less) and larger regions, because of the large number of sub-millimeter holes 100 used to achieve cosmetic effects as described herein. For example, the small size of the holes 100 generated at an areal fraction between about 5% and 50% can provide a substantially uniform dispersion of such holes 100 when viewed at size scales of about 1 cm or larger. Accordingly, the exemplary methods described herein can include directional closure of a large number of small holes 100, which can well accommodate any gradients in shrinkage that may result within or adjacent to a particular treatment region, and which may be applied in treatment regions having arbitrary shapes and extents.

After the holes 100 are formed in skin or other tissue, preferably without a continuous rigid cuff of thermally-damaged tissue 110 as described herein, it is possible to promote a closure of the holes 100 by applying appropriate lateral forces (e.g., compressive or tensile forces) to the tissue in the treated region as it heals. Such exemplary forces can facilitate contact between opposite edges of the holes 100, e.g., near the tissue surface, and increase overall shrinkage of the tissue as the holes 100 heal in a closed configuration. Further, anisotropy or directionality of the overall skin shrinkage in the treated region following formation of the holes 100 can be achieved by application of such forces in a particular direction during the subsequent healing or recovery processes.

For example, the tissue can be compressed in the direction of the arrows in FIG. 1E, and the staggered arrangement of holes 100 can facilitate "pinching" or collapse of the holes 100. A compression of the offset holes 100 in adjacent rows can lead to or facilitate closing or collapse of the various rows of the holes 100, e.g., as shown in FIG. 1G, while reducing associated deformations or stresses in the tissue between the holes 100 when the holes 100 are fully or partially squeezed closed.

Figure 3A:
FIG. 3A is a schematic side view of a stretch film in accordance with further exemplary embodiments of the present disclosure.
Figure 3B:
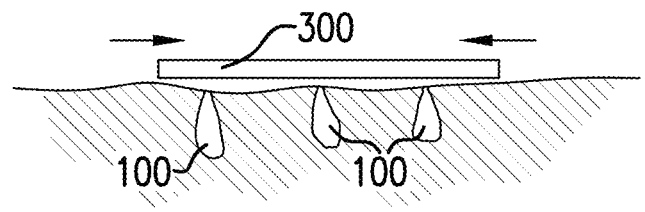
FIG. 3B is a schematic side view of the exemplary film shown in FIG. 3A being applied to the surface of a region of skin containing holes therein.

In one exemplary embodiment of the present disclosure, a stretch film 300 can be used to provide a compressive surface force to the tissue surface in the treated region and promote hole closure. For example, as shown in FIG. 3A, the film 300 can be pre-stretched in the direction of the arrows. The stretch film 300 can then be adhered to the tissue surface, as shown in the exemplary cross-sectional view of the treated region in FIG. 3B. The pre-stretched film 300 can then generate a directional compressive force along the tissue surface, as shown by the arrows in FIG. 3B. This force can pull together the edges of the holes 100, particularly near the tissue surface, to facilitate hole closure and increased shrinkage of the tissue during the healing process. For example, the film 300 can be applied such that the direction of compressive forces at the tissue surface is directed across the shorter dimension of elongated or lenticular holes 100 (e.g., in the direction of the arrows in the exemplary configuration shown in FIG. 1E).

Materials that can be used to form the film 300 include Tegaderm™, another stretchable polymer, or the like. For example, Tegaderm™ has adherent properties and can be stretched up to about 30-40% and then applied to the tissue surface. Other exemplary film materials can also be used in further embodiments. Such films can be provided with an adhesive surface, or alternatively can be adhered to the tissue surface using any appropriate biocompatible glue, cement, or adhesive.

For example, the compressive film 300 can be maintained on the tissue surface for several days, e.g. about 4 days or longer, or about 4-6 days, to facilitate sufficient healing or modification of the skin tissue while it is held in a compressed state, e.g., to minimize or prevent re-opening of the holes 100 or collagen expansion in the compressive direction by external forces.

In further exemplary embodiments, a stabilizing film 330 (shown in FIG. 3C), e.g., a non-stretching film or rigid plate or the like, can be adhered to the upper surface of the film 300 after it has relaxed and compressed the tissue surface. This stabilizing film 330 can provide a mechanical stability to the compressed tissue surface to maintain the compressive state and constrain further displacement (e.g., relaxation) of the compressed tissue during the healing process, for example, to prevent relaxation of the film 300 during the recovery process or prevent detachment of the film 300 from the skin surface. In certain exemplary embodiments, the stabilizing film can be adhered directly to the skin surface surrounding the treated region, e.g., beyond the edges of the stretch film 300, instead of or in addition to being adhered to the top of the stretch film 300.

According to yet further exemplary embodiments, a tensile force can be applied to a surface region of tissue to promote closure of holes 100 formed therein. A tensile force can be applied to the tissue in the direction of the arrows shown in FIG. 1F. Such exemplary tensile force can locally stretch the tissue in the direction of the arrows, which may cause the lateral sides of the holes to approach and/or contact each other, also as shown in FIG. 1G. Such narrowing of the holes can facilitate closure and healing, and result in local directional shrinkage of the tissue in a direction orthogonal to the applied tensile force as the holes heal.

Figure 3C:
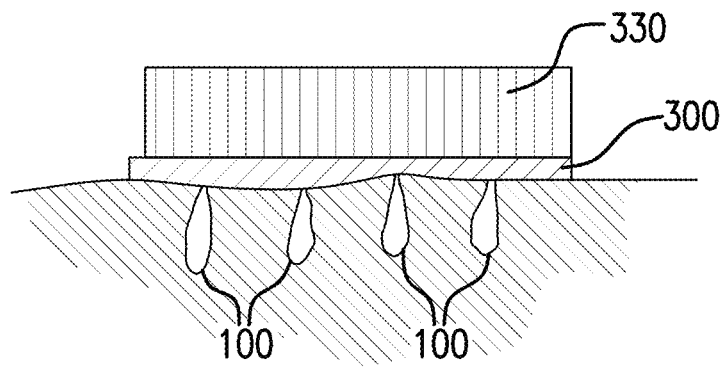
FIG. 3C is a schematic side view of the exemplary film applied to the surface of the region of skin as shown in FIG. 3B, with a rigid object adhered to the top of the stretch film to stabilize it mechanically.

The exemplary tensile force, as illustrated in FIG. 1F can be applied using any of a variety of techniques and/or devices. For example, the force can be applied manually, e.g., by pressing fingers against the skin at opposite sides of the treated area, adjacent to the perimeter thereof. The fingers can then be spread apart to apply the tensile force to the tissue, e.g., to stretch the region of tissue between the finger contact points. A rigid or non-stretchable adhesive film or plate 330, similar to that shown in FIG. 3C, can then be adhered directly to the stretched tissue surface (as opposed to being adhered to a stretch film 300 as shown in FIG. 3C) to inhibit or prevent relaxation of the tissue as the holes heal, thereby maintaining the tissue in a stretched or tensile state. In a further embodiment, a device can be used that includes two or more contact surfaces that can be spread apart, e.g., a pair of forceps or the like having a flat contact area on the end of each tip. In a similar manner, the contact areas can be pressed against the tissue and then moved apart mechanically to stretch the tissue between the contact areas. The contact areas can be provided with a rough, non-slip, and/or adhesive surface to maintain contact with particular locations on the skin or tissue surface as the tensile force is applied. Other exemplary techniques to stretch or distort the skin locally may also be used with the exemplary embodiments of the present disclosure.

Figure 4A:
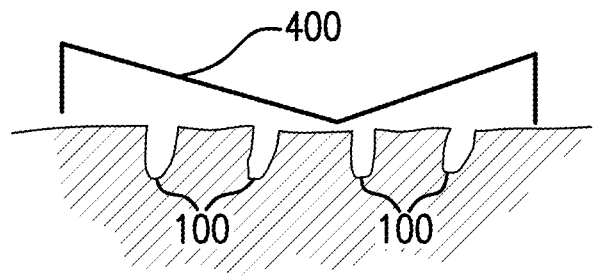
FIG. 4A is a schematic side view of a surgical staple that can be used to compress a region of skin tissue, in accordance with further exemplary embodiments of the present disclosure.
Figure 4B:
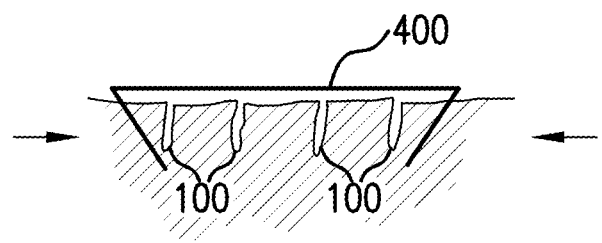
FIG. 4B is a schematic side view of the staple shown in FIG. 4A that is applied to a region of skin containing holes therein.

In another exemplary embodiment of the present disclosure, one or more surgical staples 400 can be used to apply and maintain a compressive force on the treated region, as shown in the exemplary cross-sectional views of a treated region in FIGS. 4A and 4B. An exemplary large surgical staple 400 (e.g., a staple large enough to span across a plurality of holes 100) is positioned over the treated region in FIG. 4A. FIG. 4B shows an exemplary compressive deformation of the treated region by the inserted staple 400. The exemplary staple 400 can be used to provide a general compression of the treated region of skin, thereby approximating the edges of a plurality of holes 100, as shown in FIG. 4B, rather than approximating two opposing edges of a single incision or wound (as is typically done with conventional applications of surgical staples). Such exemplary use of one or more surgical staples 400 may provide increased compression of the skin below the surface of the treated region as compared to that provided by application of a stretch film 300 to the skin surface (shown in FIG. 3B), because of the anchoring and pulling together of tissue below the surface by the staple 400.

Figure 4C:
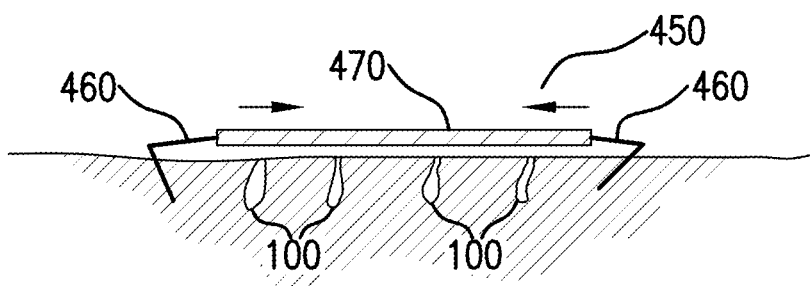
FIG. 4C is a schematic side view of a tensioning clip that is applied to a region of skin containing holes therein in accordance with certain exemplary embodiments of the present disclosure.

In another exemplary embodiment, a tensioning clip 450 as shown in FIG. 4C can be used to apply and maintain a compressive stress in the treatment region. The clip 450 can include two or more prong arrangements 460 capable of being, structured or configured to be inserted into skin. The exemplary prong arrangements 460 can have a sharp point or edge at their distal ends to facilitate penetration into the skin, and can be made from any material sufficiently rigid or strong to support a stress as described below without breaking or deforming significantly (e.g., a metal or rigid plastic or the like). The prong arrangements 460 can be connected by an elastic material 470, which can be provided as a strap, cord, or the like (e.g., similar to a rubber band, small bungee cord, or the like). The elastic material 470 can be stretched and the prong arrangements 460 then inserted into skin within and/or adjacent to the treatment region that contains holes formed as described herein. The stretched elastic material 470 can then cause the prong arrangements 460 to exert a compressive force between them, as shown by the arrows in FIG. 4C. In this exemplary manner, a compressive stress can be generated and maintained over at least a portion of the treatment area using a tensioning clip 450 that can be easily inserted into and removed from the skin. The size of the prong arrangements 460 and the elastic material 470 can be selected based on the size of the treatment region and/or portion of such region over which a stress is to be maintained.

According to certain exemplary embodiments, a plurality of staples 400 and/or tensioning clips 450 can be applied within and/or across an entire treated region, or a portion thereof. In further embodiments, staples 400 and/or tensioning clips 450 can be oriented in different directions on or across the treated region to vary the local preferred direction of shrinkage and/or to provide increased non-directional shrinkage of the treated region (e.g., as compared to a conventional fractional damage procedure that does not compress the treated region after holes 100 are formed).

The staple(s) 400 and/or tensioning clips 450, if used, can be retained in the treatment region for several days, e.g. about 4-6 days, to maintain a compressive state therein during the healing/recovery process, thereby allowing sufficient healing or modification of the skin tissue while it is held in a compressed state. Further, the staples 400 and/or tensioning clips 450 can be small or thin in at least one direction, to avoid formation of visible markings upon their removal. In certain exemplary embodiments, staples 400 and/or tensioning clips 450 can be used that are thin and/or that include several prongs configured to pierce the skin. Such staples 400 and/or tensioning clips 450 can provide compressive forces comparable to a single large staple 400 or clip 450 while allowing the individual prongs to be smaller in size to reduce or eliminate formation of markings when such staples 400 and/or tensioning clips 450 are removed.

Figure 5A:
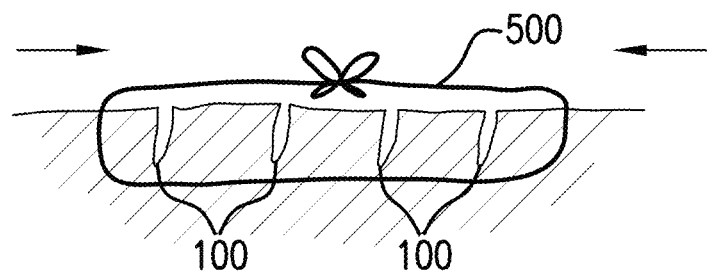
FIG. 5A is a schematic side view of a suture that can be used to compress a region of skin tissue, in accordance with further exemplary embodiments of the present disclosure.

In yet another exemplary embodiment of the present disclosure, one or more sutures 500 can be applied to the treated region apply to maintain a compressive force thereon, as shown in the exemplary cross-sectional view of FIG. 5A. Each suture 500 can be large enough to span across a plurality of holes 100, thereby promoting directional approximation of opposing surfaces of the holes 100, as shown in FIG. 5A. Similar to the staple 400 shown in FIG. 4B, the suture 500 may provide increased compression of the skin below the surface of the treated region as compared to that provided by application of a stretch film 300 to the skin surface.

Figure 5B:
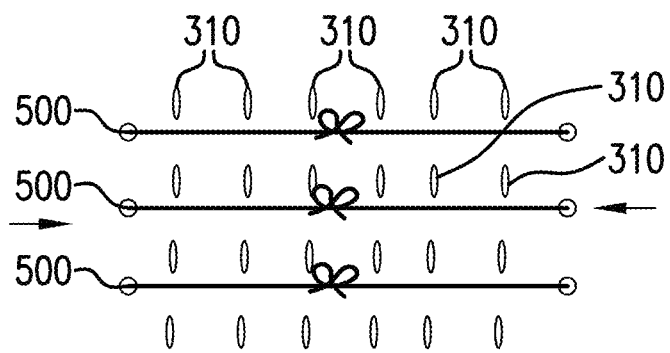
FIG. 5B is a schematic top view of the plurality of sutures such as that shown in FIG. 5A that are applied to a region of skin containing holes therein in a first exemplary configuration.
Figure 5C:
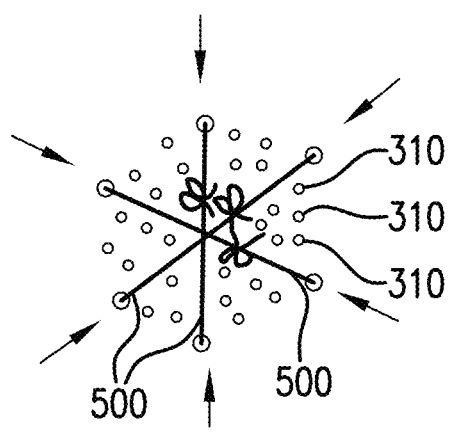
FIG. 5C is a schematic top view of the plurality of sutures such as that shown in FIG. 5A that are applied to a region of skin containing holes therein in a second exemplary configuration.

According to certain exemplary embodiments, a plurality of sutures 500 can be applied within and/or across an entire treated region, or a portion thereof. For example, a plurality of sutures 500 can be applied substantially parallel across the treated region, as shown in the exemplary top view of FIG. 5B. The arrows in FIG. 5B indicate the direction of compressive forces, and the small vertical lines 310 represent the approximated edges of the holes 100 at the skin surface. In another exemplary embodiment, the sutures 500 can be applied in different directions over the treated region, such as in the exemplary configuration shown in the top view of FIG. 5C, to provide increased nondirectional shrinkage of the treated region. The arrows in FIG. 5C represent the local direction of compressive forces, which may tend to omnidirectionally or isotropically compress the edges of the holes 100 at the skin surface. In still another exemplary embodiment, the sutures 500 can be oriented in different directions within or across the treated region to vary the local preferred direction of shrinkage within the treated region.

Similar to the stretch film 300, the staple 400, and/or the suture(s) 500, if used, can be retained in the treatment region for several days, e.g. about 4-6 days, to maintain a compressive state therein during the healing/recovery process, thereby allowing sufficient healing or modification of the skin tissue while it is held in a compressed state.

According to further exemplary embodiments, other devices and techniques can also be used to apply and maintain compressive forces to the perforated tissue in the treated region such as, e.g., forceps, adhesive heat-shrink films, surface application of curable liquids such as polymer precursors that can shrink and adhere to the skin surface as they cure, etc. Any such heat-shrink films, curable shrinking liquids, and the like that are known in the art may be used with certain embodiments of the present disclosure.

In still further exemplary embodiments, any combination of stretch film 300, staples 400, sutures 500, stretch clips 450, heat-shrink films, and/or curable liquids can be used to apply and/or maintain stresses or deformations in the treated region as the holes 100 heal.

Various additional procedures can be used to promote hole closure and healing of the holes 100 after they are ablated in the tissue. For example, the ablated holes 100 can be exposed to saline or other solutions after they are formed, to promote hydration and softening of the tissue 210 prior to healing. Such solutions can also facilitate removal of debris or impurities in the holes, e.g., removal of blood that may be present after the holes 100 are ablated as described herein.

In further exemplary embodiments, biocompatible glues or cements can be used to facilitate more rapid adherence of the closed holes 100, e.g., during the healing process. For example, photochemical tissue bonding (PTB) techniques can be used to help attach the holes 100 in a closed configuration during the healing process. In the exemplary PTB process, a photosensitizer (e.g., rose bengal, riboflavin, porphyrins, chlorins, and the like) can be applied to the tissue after the holes 100 have been formed therein, but prior to applying the compressive film 300 or a tensile or compressive force as described herein. Photosensitizer precursors including, e.g., pro-drugs of such photosensitizers, can also be used, where such precursors may be metabolized or otherwise activated to form photosensitizers in the tissue. Such photoactive substances (e.g., photosensitizers or precursors) can promote tissue bonding when applied to tissue, optionally activated or allowed to metabolized, and then exposed to light having one or more appropriate wavelengths.

After the holes 100 are directionally compressed using the stretch film 300, staple(s) 400, suture(s) 500, and/or other compressive or tensile forces, the tissue can be exposed to light having an appropriate wavelength to activate the tissue bonding, to promote adhesion of the hole walls within a few minutes. The choice of wavelength can be based on the particular photosensitizer or precursor used. The compressive film 500 can then be removed while the holes 100 remain closed at the tissue surface and continue to heal.

According to yet further exemplary embodiments, the stretch film 300 can be provided with a layer of one or more photosensitizers or precursors, such that at least a portion of the photoactive substance(s) is transferred onto the tissue surface when the film 300 is applied to the surface of the tissue. For example, the photoactive substance(s) can be provided in a gel or micro-encapsulated layer on the surface of the film 300 that is placed against a skin surface. The activating light can then be directed through the top surface of the film 300 and onto the compressed tissue surface and the photoactive substance applied thereon. In general, one or more of the various conventional photochemical tissue bonding systems, materials, and methods can be used to facilitate more rapid hole closure in accordance with embodiments of the present disclosure.

In further exemplary embodiments, other tissue glues such as, e.g., cyanoacrylates, can be used to glue the holes 100 together after they are formed and compressed, stretched and/or closed. It may be preferable to limit application of such glue to the tissue surface and avoid introduction of them within the holes 100, to avoid filling them with unwanted material that may inhibit subsequent hole closure and shrinkage. The use of any conventional tissue-bonding techniques or tissue glues, including those described herein, can reduce the amount of time that the compressive film 300 or other dressings are maintained over the treated tissue area as it heals, while preventing re-opening of the closed holes 100 during the gradual healing process.

As described herein, the shape, density or spacing, and pattern or spatial distribution of the holes 100, and/or the orientation of an applied compressive or tensile force to the surface of the treated region, can provide a directionally-oriented shrinkage of the tissue as it heals. Such directionality can be utilized to achieve improved cosmetic results by generating increased shrinkage in a preferred local direction in an ablative fractional resurfacing procedure. A plurality of such procedures can be applied to a particular treated region to obtain greater overall shrinkage of the skin or other tissue, preferably allowing sufficient healing time between subsequent treatments on a particular area. The compressive and/or tensile directions can be varied in different treatments of a single area to obtain a more homogenous shrinkage of tissue in the area. The sizes and preferred shrinkage directions of adjacent treated regions can also be selected and varied to achieve desirable overall shrinkage patterns for the skin or other tissue.

An application of a tensile or compressive force to the tissue to promote hole closure can also affect the characteristics of collagen that may be formed during the hole closure and tissue healing processes that occur after the holes 100 have been formed. For example, collagen may grow and/or align in particular directions when forming in tissue that is deformed by application of external forces after the formation of the holes 100, as described herein. Such modification of collagen growth and/or alignment in the treated tissue may provide further desirable cosmetic effects.

Figure 6:
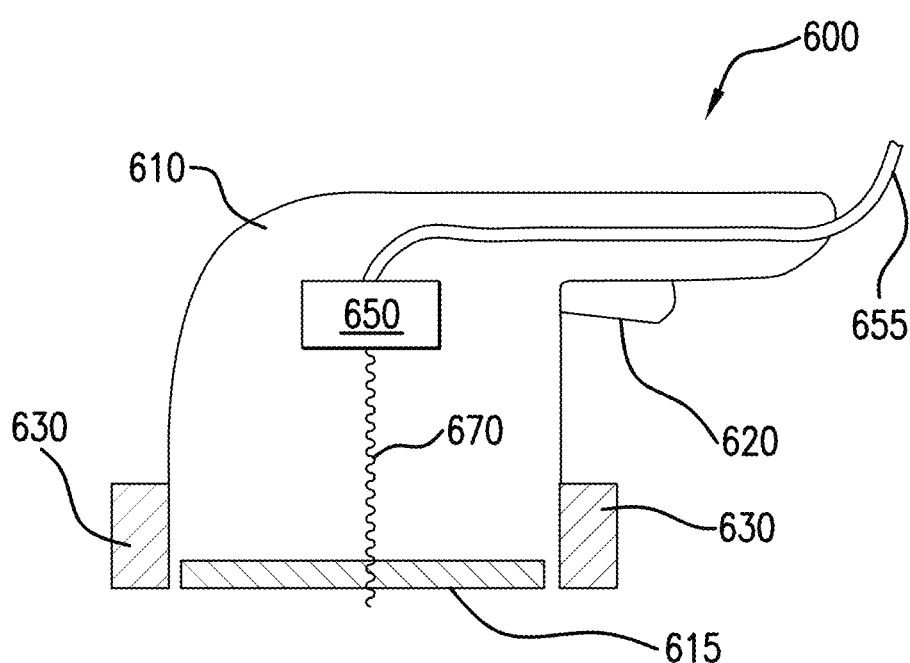
FIG. 6 is a schematic side view of an exemplary apparatus for optically ablating fractional damage in tissue and providing a compressive stress to the tissue, in accordance with further exemplary embodiments of the present disclosure.

In further exemplary embodiments of the present disclosure, a system 600 can be provided to ablate a plurality of the holes 100 in a treated region of skin using optical energy 670, and then apply a compressive or tensile force to the treated region. For example, an exemplary system 600 can be provided that includes a handpiece 610 having a window 615 on a lower portion thereof, an optical energy arrangement 650, an actuator 620, and a compression arrangement 630, as shown in FIG. 6. In certain embodiments, the system 600 can include a waveguide 655, e.g., one or more optical fibers, a hollow fiber waveguide, or the like, which can be configured to direct optical energy 670 from an external source (not shown), such as a laser, to the optical arrangement 650 and onto the skin being treated. In further exemplary embodiments, the optical energy source (not shown) may be provided within the handpiece 610.

The window 615 can be configured and/or structured to be placed on the surface of a region of skin to be treated. In certain embodiments, the window 615 can be a plate or lens that is optically transparent to the wavelength(s) of optical energy 670 being used to ablate the holes 100. For example, the window 615 can include or be made of zinc selenide if the source of optical energy 670 is a $CO_2$ laser. The window 615 can include or be made of sapphire if the source of optical energy 670 is an Er:YAG laser. The lower surface of the window 615, which can be configured to contact the tissue surface during operation of the system 600, can be planar in shape. In certain embodiments, this lower surface may be rounded, e.g., cylindrical, ellipsoidal, or spheroidal in shape, which may enhance the local force of the window 615 on the tissue surface when the exemplary system 600 is applied to the treatment region during ablation of the holes 100.

In certain exemplary embodiments, the window 615 can be absent, e.g., if an optical energy source such as an excimer laser is used. An excimer laser can ablate holes in skin tissue with little or no thermal cuff formed, and applying a window on the tissue surface while the holes are ablated, to disrupt any thermal cuff, may not be needed.

The actuator 620 can be configured to activate the optical energy source and the optical arrangement 650 to direct optical energy 670 onto the skin tissue below the handpiece 610 and ablate a plurality of holes 100. The optical arrangement 650 can include one or more translators, reflecting elements such as mirrors or the like, etc., which can be configured to direct the optical energy 670 in a particular spatial and temporal pattern to form a predetermined pattern of holes 100. Such arrangements are known in the art and can be found in conventional ablative fractional resurfacing systems.

The exemplary system 600 can be applied onto a treatment region until the lower surface 615 of the system 600 contacts the skin surface, and the actuator 620 can then be activated to ablate a plurality of holes 100 in the skin. The size, density, and pattern of ablated holes can be predetermined, e.g., using a conventional control arrangement (not shown) that can be configured to control various parameters such as power and duration of the optical energy source, operation of the optical arrangement 650, etc. The exemplary system 600 can be further adapted or configured to activate the compression arrangement 630 to apply a compression element to the treated region after the holes 200 have been ablated in the treated region.

In one exemplary embodiment, the compression arrangement 630 can include a surgical stapler configured to be mechanically or electrically actuated by the actuator 620, such that one or more large staples 400 and/or tensioning clips 450 are applied across at least a portion of the treated region as described herein above.

According to another exemplary embodiment, the compression arrangement 630 can include a suture needle (e.g. a curved needle) and suture thread. The compression arrangement 630 can be capable of or configured for introducing one or more lengths of suture thread below the surface of the treated region, e.g., with the ends of the thread protruding from the surface of the skin, when it is actuated by the actuator 620, after the needles 200 are withdrawn from the treatment site. The ends of the suture thread can then be tied together to form a suture 500 that can apply a compressive force to the skin tissue in the treated region as described herein above. Optionally, the compression arrangement 630 can be capable of or configured for tying off the suture thread when actuated, e.g., at a preselected tension.

In yet another exemplary embodiment, the compression arrangement 630 can include a stretch film applicator that is capable of and/or configured for adhering a stretch film 300 or the like over the treated region after the holes 100 are ablated in the skin. For example, the compression arrangement 630 can include a small roll of stretch film 300 configured similar to a packing tape dispenser. The system 600 can be translated over the treated region after the holes 100 are ablated, to apply the film 300 over the holes 100 just formed. The film 300 can also be provided in pre-cut pieces that are sized to fit over the treated region.

According to a further exemplary embodiment, the compression arrangement 630 can include a reservoir of a curable coating material, as described herein above, and it can be capable of and/or configured for applying such coating material to the surface of the treated region after holes 100 are ablated in the skin. In another exemplary embodiment, the compression arrangement 630 can be configured or adapted to apply a photoactivated material (or precursor of such material), as described herein above, to at least a portion of the treated region, and directing light energy onto the region to activate the material. Exemplary embodiments of the system 600 in which the compression arrangement 630 is capable of applying or configured to apply other types of compression or tensioning elements to the treated region after the holes 100 are formed also fall within the scope of the present disclosure.

EXAMPLE

Figure 7A:
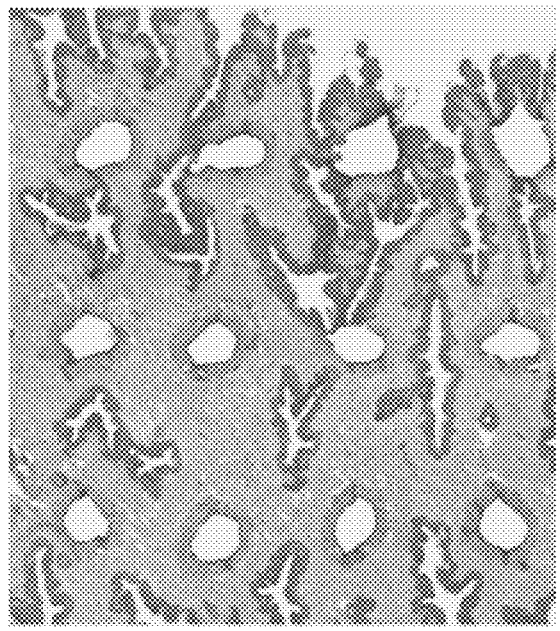
FIG. 7A is a exemplary histological image of fractionally ablated skin and associated thermal cuffs generated by a $CO_2$ laser without any contact plate.

An exemplary procedure was performed in accordance with certain exemplary embodiments of the present disclosure, using a $CO_2$ laser to ablate a plurality of holes in samples of ex vivo human skin samples. A histological image of fractionally ablated skin generated without any contact plate (e.g., similar to a conventional ablative fractional resurfacing procedure) is shown in FIG. 7A. A cuff of thermally-damaged tissue, similar to the 'cuff' 110 shown in FIG. 1A, can be seen as a slightly darkened uniform layer around each rounded hole in this figure.

Figure 7B:
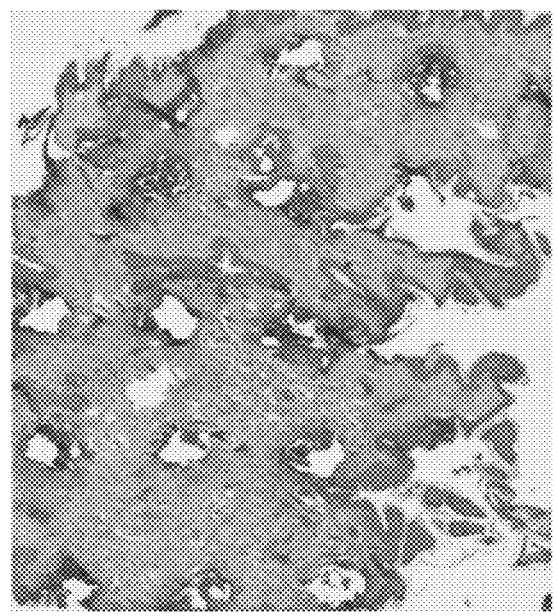
FIG. 7B is an exemplary histological image of fractionally ablated skin with disrupted thermal cuffs generated by a $CO_2$ laser with an overlying contact plate.

An ablative fractional procedure was also performed using a transparent plate held against the sin surface during the ablation of the holes, as described herein. A histological image of the ex vivo skin tissue after this treatment is shown in FIG. 7B. The plate was pressed onto the skin surface with sufficient force (about 67 N) to prevent vaporized material from escaping through the top opening of the holes as they were formed. As compared to the conventional ablated holes shown in FIG. 7A, the small holes formed in a 'constrained' ablative procedure appear to be less rounded and less regular in shape. The darker layer of thermally damaged material appears to be broken up and missing in some locations on the hole perimeters in FIG. 7B, in contrast to the more uniform thermal "cuff" visible in FIG. 7A. The lack of a uniform, rigid cuff of thermally-damaged tissue around the ablated holes illustrated in FIG. 7B suggests that the formation of ablated holes using a plate applied to the skin surface can provide holes that are more easily closed, optionally in a particular local direction, to facilitate an increased overall skin area reduction in accordance with the exemplary methods and apparatus described herein.

It will thus be appreciated that those skilled in the art will be able to devise numerous systems, arrangements and methods which, although not explicitly shown or described herein, embody the principles of the present disclosure and are thus within the spirit and scope of the present disclosure. In addition, all publications, patents, and patent applications referenced herein are incorporated herein by reference in their entireties.

What is claimed is:

1. A cosmetic method for producing an effect in skin tissue, comprising:
    ablating a plurality of holes in a region of the skin tissue using electromagnetic radiation through an optically transparent plate;
    during the ablation procedure, disrupting a formation of a thermal cuff around the holes using the optically transparent plate;
    causing a stress that is at least one of a compressive stress or tensile stress in the region of the skin tissue after ablating the holes, the stress being caused by applying a pre-stretched film material on the skin tissue which includes the region; and
    applying a rigid non-stretchable material on the pre-stretched film material after the pre-stretched film material reaches a relaxed state so as to maintain the stress in the region of the skin tissue, the rigid non-stretchable material being a rigid non-stretchable film or a rigid non-stretchable plate, wherein a diameter of the holes is less than 1 mm,
    wherein the holes extend from a surface of the skin tissue into a dermal layer of the skin tissue,
    wherein the holes extend over an areal fraction of a surface of the region that is between 5% and 50%,
    wherein the stress provides a force in the region along a direction that is parallel to the surface of the region, and
    wherein the stress is maintained on the surface of the region until the holes have closed.

2. The method of claim 1, further comprising pressing an optically transparent window over a location of at least one of the holes while the at least one of the holes is being ablated.

3. The method of claim 1, wherein a diameter of the holes is between 0.1 mm and 0.5 mm.

4. The method of claim 1, wherein the holes extend over the areal fraction of the surface of the region that is between 10% and 30%.

5. The method of claim 1, wherein the stress is the compressive stress, and wherein the pre-stretched film material adhered over at least one portion of the region.

6. The method of claim 5, wherein, in the applying procedure, the rigid non-stretchable material is the rigid non-stretchable film that is adhered onto the pre-stretched film material after the pre-stretched film material has been adhered to the at least one portion of the region.

7. The method of claim 1, wherein the stress is the compressive stress, which is provided in addition to the pre-stretched film material by inserting at least one of at least one surgical staple or at least one suture into or adjacent to the region.

8. The method of claim 1, wherein the stress is the compressive stress, which is provided in addition to the pre-stretched film material by applying a heat-shrink film onto at least a portion of the region and then heating the heat-shrink film.

9. The method of claim 1, wherein the stress is the compressive stress, which is provided in addition to the pre-stretched film material by applying a curable liquid onto at least a portion of the region and allowing the liquid to cure, wherein the curable liquid is a liquid that shrinks when curing.

10. The method of claim 1, wherein the stress is the tensile stress, which is provided in addition to the pre-stretched film material by stretching at least a portion of the region, and then adhering a rigid object onto the stretched portion of the region.

11. The method of claim 1, wherein the stress is the compressive stress, and wherein the compressive stress is maintained for at least 4 days.

12. The method of claim 1, further comprising applying a photoactivated substance to at least one portion of the region, and directing light energy onto the region while maintaining the stress until the adhesive has been activated.

13. A system for producing a cosmetic effect in skin tissue, comprising:
   a handpiece;
   an optical arrangement including through an optically transparent plate which is structured or configured to direct at least one beam of ablative energy onto a plurality of locations in a region of the skin tissue to ablate a plurality of holes therein;
   a compressing arrangement configured to cause and maintain a compressive stress over at least a portion of the region after the holes are formed, wherein the compression arrangement comprises a pre-stretched film material configured to be provided on the skin tissue which includes the region; and
   a rigid non-stretchable material which, in operation, is provided on the pre-stretched film material after the pre-stretched film material reaches a relaxed state so as to maintain the stress in the region of the skin tissue, the rigid non-stretchable material being a non-stretchable film or a non-stretchable plate,
   wherein, during the ablation of the holes, the optically transparent plate is positioned to disrupt a formation of a thermal cuff around the holes,
   wherein the optical arrangement is configured to generate the at least one beam of ablative energy with a diameter that is less than 1 mm,
   wherein the plurality of holes extend over an areal fraction of a surface of the region that is between 5% and 50%,
   wherein the optical arrangement comprises at least one of a fiber optic delivery arrangement, a translator, or a reflecting element, and is configured to cause the at least one beam to form the holes that extend from a surface of the skin tissue into a dermal layer of the skin tissue, and
   wherein the compressive arrangement is configured to maintain the compressive stress that provides a force in the region along a direction that is parallel to the skin surface until the holes have closed.

14. The system of claim 13, wherein the diameter of the at least one beam of ablative energy is between 0.1 mm and 0.5 mm.

15. The system of claim 13, further comprising an optically transparent window configured or structured to be pressed onto the plurality of locations while the holes are being ablated.

16. The system of claim 13, wherein the ablative energy is provided by an ablative laser.

17. The system of claim 13, wherein the system is configured to ablate the holes that extend from the surface of the skin tissue through the entire dermal layer of the skin tissue.

18. The system of claim 13, wherein the pre-stretched film material is configured to adhere to at least a portion of the region of the skin tissue.

19. The system of claim 18, wherein the rigid non-stretchable material is the rigid non-stretchable film that is configured to be adhered onto the pre-stretched film material after the pre-stretched film material has been adhered to at least a portion of the stressed region of the skin tissue.

* * * * *